(12) United States Patent
Marton

(10) Patent No.: US 10,100,416 B2
(45) Date of Patent: Oct. 16, 2018

(54) PLASMA-ARC-THROUGH APPARATUS AND PROCESS FOR SUBMERGED ELECTRIC ARCS WITH VENTING

(71) Applicant: MagneGas Corporation, Clearwater, FL (US)

(72) Inventor: Scott Marton, Clearwater, FL (US)

(73) Assignee: MagneGas Corporation, Clearwater, FL (US)

( * ) Notice: Subject to any disclaimer, the term of this patent is extended or adjusted under 35 U.S.C. 154(b) by 304 days.

(21) Appl. No.: 15/230,537

(22) Filed: Aug. 8, 2016

(65) Prior Publication Data

US 2016/0340790 A1    Nov. 24, 2016

Related U.S. Application Data

(63) Continuation of application No. 14/288,807, filed on May 28, 2014, now Pat. No. 9,433,916.

(51) Int. Cl.
| | |
|---|---|
| *C25B 1/02* | (2006.01) |
| *C25B 1/04* | (2006.01) |
| *B01J 19/08* | (2006.01) |
| *C10J 1/26* | (2006.01) |
| *A61L 9/00* | (2006.01) |
| *C10L 3/00* | (2006.01) |

(Continued)

(52) U.S. Cl.
CPC ..................... *C25B 1/02* (2013.01); *A61L 2/00* (2013.01); *A61L 9/00* (2013.01); *B01J 19/088* (2013.01); *C10J 1/26* (2013.01); *C10L 3/00* (2013.01); *C25B 1/00* (2013.01); *C25B 1/04* (2013.01); *C25B 9/06* (2013.01); *C25B 11/12* (2013.01); *C25B 15/02* (2013.01); *B01J 2219/082* (2013.01); *B01J 2219/083* (2013.01); *B01J 2219/0805* (2013.01); *B01J 2219/089* (2013.01); *B01J 2219/0809* (2013.01); *B01J 2219/0815* (2013.01); *B01J 2219/0839* (2013.01); *B01J 2219/0869* (2013.01); *B01J 2219/0871* (2013.01); *B01J 2219/0877* (2013.01); *B01J 2219/0894* (2013.01); *C10J 2300/1238* (2013.01); *C10L 2290/38* (2013.01); *Y02E 60/366* (2013.01)

(58) Field of Classification Search
CPC .. C25B 1/02; C25B 1/04; B01J 19/088; B01J 2219/0805
See application file for complete search history.

(56) References Cited

U.S. PATENT DOCUMENTS

| | | |
|---|---|---|
| 603,058 A | 4/1898 | Eldridge |
| 5,159,900 A | 11/1992 | Dammann et al. |

(Continued)

*Primary Examiner* — Nicholas A Smith
(74) *Attorney, Agent, or Firm* — Larson & Larson, P.A.; Frank Liebenow; Justin P. Miller

(57) ABSTRACT

An application for a recycler includes a pressure and temperature resistant metal vessel that is filled with a liquid. Within the vessel is at least one submerged electric arc between a pair of electrodes (e.g. carbon based electrodes) powered by either a DC or AC current. The electric arc produces a combustible gas as the liquid is pumped through a bore in one or both of the electrodes, delivering the liquid directly to the location of the arc, thereby reducing or eliminating any ignition of the gas by the arc. Should ignition occur, at least one vent in the electrode(s) or electrode holder(s) vents pressure from within the bore to the vessel area outside of the electrode(s).

20 Claims, 5 Drawing Sheets

(51) Int. Cl.
   *C25B 1/00* (2006.01)
   *C25B 9/06* (2006.01)
   *C25B 11/12* (2006.01)
   *C25B 15/02* (2006.01)
   *A61L 2/00* (2006.01)

(56) References Cited

U.S. PATENT DOCUMENTS

| | | |
|---|---|---|
| 5,417,817 A | 5/1995 | Dammann et al. |
| 5,435,274 A | 7/1995 | Richardson, Jr. |
| 5,692,459 A | 12/1997 | Richardson, Jr. |
| 5,792,532 A | 8/1998 | Richardson, Jr. |
| 6,183,604 B1 | 2/2001 | Santilli |
| 6,540,966 B1 | 4/2003 | Santilli |
| 6,663,752 B2 | 12/2003 | Santilli |
| 6,673,322 B2 | 1/2004 | Santilli |
| 6,926,872 B2 | 8/2005 | Santilli |
| 8,236,150 B2 * | 8/2012 | Santilli .................. B01J 19/088 204/275.1 |

* cited by examiner

PLASMA-ARC-THROUGH APPARATUS AND PROCESS FOR SUBMERGED ELECTRIC ARCS WITH VENTING

CROSS-REFERENCE TO RELATED APPLICATION

This application is a continuation of U.S. patent application Ser. No. 14/288,807 filed May 28, 2014. This application is related to U.S. Pat. No. 6,540,966 issued Apr. 1, 2003. This application is also related to U.S. Pat. No. 7,780,924 issued Aug. 24, 2010. This application is also related to U.S. Pat. No. 6,673,322, issued Jan. 6, 2004. This application is also related to U.S. Pat. No. 8,236,150, issued Aug. 7, 2012. The disclosure of the above patents is hereby incorporated by reference.

FIELD

This invention relates to the field of production of a clean burning, cost competitive combustible fuel via submerged electric arcs between electrodes (e.g. carbon electrodes). Specifically, the invention provides an apparatus and methods to direct a flow of a liquid (feedstock) through the plasma surrounding the tip of the electrodes while controlling back pressure due to combustion (micro explosions) of the combustible fuel.

BACKGROUND

Examples of prior art in the field are given by U.S. Pat. No. 603,058 to H. Eldridge; U.S. Pat. No. 5,159,900 to W. A. Dammann et al; U.S. Pat. No. 5,435,274 to W. H. Richardson, Jr.; U.S. Pat. No. 5,417,817 to W. A. Dammann et al; U.S. Pat. No. 5,692,459 to W. H. Richardson, Jr.; U.S. Pat. No. 5,792,325 to W. H. Richardson, Jr. U.S. Pat. Nos. 6,926,872, 6,673,322, 6,663,752, 6,540,966, and 6,183,604, all issued to Rugerro Maria Santilli describe other approaches to these problems and other problems.

Submerged electric arcs were discovered over 150 years ago by sailors soon after the first constructions of metal ships. The combustible character of the gas produced by submerged electric arcs was discovered at the same time by sailors assisting the submerged operators; the ignored bubbles of gas reaching the water surface being referred by reports of the time as "fire on water." Consequently, both submerged electric arcs and the combustible nature of the gas they produce are well known.

About one century ago attempts were initiated for the industrial production of the combustible gas produced by submerged electric arcs. Despite numerous efforts, no industrial and/or consumer utility emerged because the production of the combustible gas resulted to be very inefficient, thus excessively expensive, and suffered from serious environmental problems.

The efficiency in the art herein considered is generally given by the numerical value of the volume or calorific heat of the gas produced divided by the electric energy used for its production. The efficiency of conventional submerged electric arc is very low for several reasons. To begin, the electric arc is indeed very efficient for the separation of water molecules into hydrogen and oxygen atoms. Further reducing the efficiency is the latter recombination of the hydrogen and oxygen into water when the hydrogen and oxygen are contained in a plasma traversed by the electric arc combusting the hydrogen in an oxygen rich environment. In fact, the primary origin of the majestic glow of submerged electric arcs is not given by the arc itself, but rather by the recombination of hydrogen and oxygen into water. Additional reasons for the inefficiency of conventional submerged electric arcs are given by the loss of power caused by the electric resistance of carbon electrodes, particularly when in the dimension needed for a sufficient operational life.

In more recent decades the industrial production of a combustible gas via submerged electric arcs was considered again, but an additional problem emerged, this time of environmental nature. As it is well known, one of the biggest environmental problems afflicting our planet is the "global warming" caused by a disproportionate increase of carbon dioxide, $CO_2$, in our atmosphere; estimated to be of the order of one million tons of $CO_2$ per day as a result of the daily operation of an estimated number of about one billion cars, one million trucks, one hundred thousand planes, plus an unknown number of agricultural, industrial and military vehicles.

The serious environmental problem here considered is that the arc first creates around the tips of the electrodes a plasma composed by mostly ionized atoms of hydrogen, oxygen and carbon. The great affinity of carbon and oxygen then creates carbon monoxide, CO, with the release of heat. The residual hydrogen recombines into the hydrogen molecule $H_2$ with the release of additional heat.

However, CO is combustible and, when in an oxygen rich plasma traversed by the electric arc, CO is turned into $CO_2$ by providing a third source of heat. Consequently, the combustible gas produced by underwater electric arcs between carbon electrodes is generally composed by $H_2$, CO, $CO_2$, $H_2O$ and other gases. The alarming environmental problem here considered is that up to 25% of $CO_2$ has been measured in the exhaust of said combustible gas, compared to about 5%-7% $CO_2$ emission for gasoline operated cars. Hence, a widespread automotive and other uses of the resulting combustible gas releases a substantial amount of $CO_2$ in the combustion exhaust.

Many of the above problems were resolved by U.S. Pat. No. 6,450,966 to Rugerro Maria Santilli, "Apparatus and Method for Recycling Contaminated Liquids", discloses a continuous flowing of the liquid (feedstock) though the electric arc. Such a flow prevents much of the separated hydrogen and oxygen from recombining into water, thus permitting a dramatic increase of the efficiency on the order of about ten times that of stationary electric arcs therefore achieving sufficient efficiency for industrial and consumer utility. Additionally, the methods and apparatus also removes the various combinations of carbon and oxygen in single, double and triple valence bonds immediately following their creation, greatly reducing percentages of $CO_2$ in the gaseous fuel produced.

The combustible gas produced by the process of '966 is currently produced and sold commercially. Such gas is clean because it generally contains no hydrocarbons due to the extreme temperature at which the gas is produced. Also, CO is a minor component of the combustible gas, rather than a byproduct of the combustion as is the case for fossil fuels. Hence, the presence of CO in an exhaust of a combustion engine using the produced gas is similar to the presence of gasoline in the exhaust of a gasoline fueled combustion engine, thus denoting in both cases incomplete or improper combustion. Additionally single bond C—O and double bond C═O contained in the gas are unstable and decompose under the combustion temperature releasing breathable oxygen in the exhaust. In fact, numerous measurements have established that, under full combustion, the combustion exhaust of the gas has no appreciable hydrocarbons or toxic substances such as carbon monoxide, CO, or nitrogen oxides, NOx, while being essentially comprised of 50%-55% water vapor, 12%-14% oxygen, 5%-7% carbon dioxide the rest being other atmospheric gases.

The '966 process resolved the basic problems of submerged stationary electric arcs but a need exists to achieve sufficient operating life of the consumable carbon electrodes prior to their replacement, as well so as to achieve a competitive cost for the gaseous fuel produced by this process making it attractive for industrial and consumer utility.

U.S. Pat. No. 6,926,872 addresses the issue of operating life using a number of configurations of durable carbon-base electrodes. A main problem in the production of clean burning gases from a submerged electric arcs is that it is not possible to use tungsten electrodes since they would melt almost instantly under 50 KW or higher power even when having substantial outer dimensions. Being such, carbon-base electrodes are the only electrodes known that are capable of withstanding the very high temperature of the submerged electric arc that reaches around 10,000 degrees Fahrenheit when powered with 100 KW.

Carbon-base electrodes are rapidly consumed, both in the delivery of high electric currents, and by consumption that is necessary to provide the carbon needed for the stability of the produced gaseous fuel. For instance, a DC electric arc between 1" diameter carbon-base rod electrodes within water or water soluble liquid (feedstock) that is powered by a 50 KW DC generator generally consumes the positively charged cathode at the rate of about 1 linear inch per minute, corresponding to the consumption of about 0.76 cubic inches of carbon per minute or about 47 cubic inches of carbon per hour. A 50 KWH system generally produce 500 standard cubic feet (SCF) (cubic feet at atmospheric pressure) of combustible gas per hour, the consumption of carbon per cubic foot of the produced gas is in the order of 0.1 cubic inch of carbon per standard cubic foot of gas produced. The above consumption is dramatically reduced when the liquid (feedstock) is rich in carbon, such as oils or oil wastes. In all cases, the consumption of the negatively charged anode is generally minimal at around less the one tenth of the consumption of the cathode.

The problem of a durable configuration of the carbon electrodes has been addressed by U.S. Pat. No. 603,058 to H. Eldridge; U.S. Pat. No. 5,159,900 to W. A. Dammann et al; U.S. Pat. No. 5,435,274 to W. H. Richardson, Jr.; U.S. Pat. No. 5,417,817 to W. A. Dammann et al; U.S. Pat. No. 5,692,459 to W. H. Richardson, Jr.; U.S. Pat. No. 5,792,325 to W. H. Richardson, Jr. Nevertheless, all these configurations are afflicted by one or another of the following insufficiencies:

1) Inability of delivering high power to the electrodes (e.g. on the order of 500 KW or more). This limitation is addressed somewhat in the prior art using the copper rods to deliver power to electrodes that rotate to achieve a longer life. In some systems, the rotation forces the delivering of power via sliding contacts that, as such, have notorious limitation in power delivery due to micro arcs, abrasion, and other problems.

2) Inability to effectively enclose the incandescent area surrounding the electric arc. This inability is not addressed in the prior art due to structural differences between the anode and cathode. This limitation carries severe shortcomings in the utility of the invention. For instance, as discussed in U.S. Pat. No. 6,450,966, it is impossible to recycle city, farm or ship sewage with an electric arc unless the incandescent area is enclosed by suitable skirt. In absence of the skirt, there is always a portion of the sewage that is not exposed to the plasma of the electric arc and, therefore, such a system is incapable of fully sterilizing the liquid.

3) Inability to reach high pressure and temperature. In much of the prior art, copper rods that deliver the power to the electrodes passes through seals in order to penetrate inside the apparatus. In turn, such a configuration is inoperative at large pressure because the force of the pressure on the copper rods is so strong that it prevents the instantaneous micrometric motions necessary for the control of the electric arc. The same configurations often fail at high temperatures, such as those over 500 degrees F., due to the consequential failure of the seals. These limitations are rather serious because the efficiency of the apparatus increases dramatically with the increase of the operating pressure since the size of the bubbles of the gas surrounding the arc is reduced with pressure. This results in increasing of the travel of the arc through the liquid (feedstock). The efficiency of the apparatus also increases with the increase of the operating temperature because the arc first evaporates the liquid (feedstock), then separates the liquid molecules and then forms a plasma with their ionized atomic constituents. Consequently, operations at sufficiently high temperatures reduces the use of electric energy for evaporation with a consequential increase of the efficiency and reduction of costs.

U.S. patent application Ser. No. 11/474,687 filed on Jun. 26, 2007, by the inventor improves upon the prior art by disclosing an apparatus permitting: 1) the desired long electrode life of the order of weeks of continuous use prior to electrode replacement, 2) effective enclosure of the incandescent area of the electrodes to permit recycling of sewage (e.g. city, farm or ship) with sterilization; 3) delivery of very high electric power to the electrodes; 4) minimization of the power loss due to the minimal travel of the electric current through the electrodes despite the size of the electrodes; 5) production of the combustible gas at any desired pressure in order to eliminate the use for expensive compressed storage of the produced gas, for instance, to directly fill up an automotive tank; 6) achievement of high operating temperatures (e.g. of the order of 1,500 degrees F.) so as to permit the utilization of the heat produced by the apparatus for the production of steam via a heat exchanger that, in turn, can be used for the production of "green electricity," (electricity meeting the environmental specifications according to the Kyoto Accord); and 7) automation in the extraction of the electrodes for easiness of service as well as complete automation of the operation and optimal use of the electrodes.

Despite these advances, a limitation exists of not entirely flowing the liquid through the gap of the electrodes, resulting in only part of the liquid being exposed to the incandescence of the electrode tips. This limits the efficiency, namely, the volume of liquid waste recycled for a given power input. This is evidently due to the fact that the produced combustible fuel exits rather violently from the gap between the electrodes, thus preventing the liquid (feedstock) from full flow-through penetration within the gap.

Furthermore, when the feedstock is subject to the plasma of the arc, the produced combustible fuel exits rather violently from the gap between the electrodes. Some of the combustible fuel ignites creating pressure waves.

What is needed is an apparatus and process that passes a liquid (feedstock) through a bore in one or both electrodes of an arc, while absorbing pressure waves created by combustion of some of the produced fuel, thus maximizing efficiency and utility.

SUMMARY

A pressure and temperature resistant metal vessel is filled with a liquid. In an interior of the vessel is at least one submerged electric arc between a pair of electrodes (e.g. carbon electrodes or other) powered by DC or AC current. The vessel has conductors for delivering an electric current to the electrodes, thereby separating the molecules of the liquid (feedstock) and causing incandescence at the tips of the electrodes. The vessel preferably, though not required, has mechanical systems that automatically (optionally remotely) maintain and optimize the electric arc. In some embodiments, the vessel has mechanical systems that automatically (optionally remotely) collect and/or compress the produced combustible fuel (gas). In some embodiments, the vessel has mechanical systems that automatically (optionally remotely) process and sterilize the liquid (feedstock). In some embodiments, the vessel has a cooling system for maintaining of the vessel at a constant temperature. In some embodiments, the vessel has mechanical systems that automatically (optionally remotely) refill the vessel with the liquid (e.g. waste to be recycled). In some embodiments, the vessel has monitoring systems for the automatic halting of all operations in the event of malfunctions or irregular values of pressure, temperature, flow, etc. In some embodiments, the vessel has a system for the automatic paging of the operator in the event of a malfunction. The pressure and temperature resistant metal vessel is also called a Recycler. In a preferred embodiment, the electrodes and/or electrode holders include vents.

In one embodiment, an apparatus for producing usable energy is disclosed including a pressure and temperature resistant vessel filled with a liquid with two electrodes held within the vessel and submerged within the liquid. A bore passes through a first electrode of the two of electrodes such that the liquid flows through the bore and exits the bore at an arc which is formed by an electric current provided between each of the two electrodes. At least one vent if formed, interfacing the bore to the area within the vessel. A combustible gas is produced by the arc and percolates to the surface of the liquid for collection.

In another embodiment, a method of producing a combustible gas is disclosed including at least partially filling a pressure and temperature resistant vessel with a liquid. The vessel has a first electrode and a second electrode held within and submerged within the liquid. The first electrode has a bore passing through the first electrode. At least one vent allows of the liquid to exit the bore. An electric current is delivered to the electrodes, creating an arc between the first electrode to the second electrode and the liquid is pumped through the bore, exiting the bore at the arc where a combustible gas is produced by the arc and collected after the combustible gas percolates to the surface of the liquid.

In another embodiment, a method of producing a combustible gas is disclosed including at least partially filling a pressure and temperature resistant vessel with a liquid. The vessel has two electrodes held by two electrode holders within the vessel and submerged within the liquid. A bore passes through a first electrode of the two of electrodes and through an associated first electrode holder of the two electrode holders, such that the liquid flows through the bore and exits the bore at the arc formed between the two electrodes. There is at least one vent. A combustible gas is produced by the arc and the combustible gas percolates to the surface of the liquid for collection

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figures 1A, 1B:
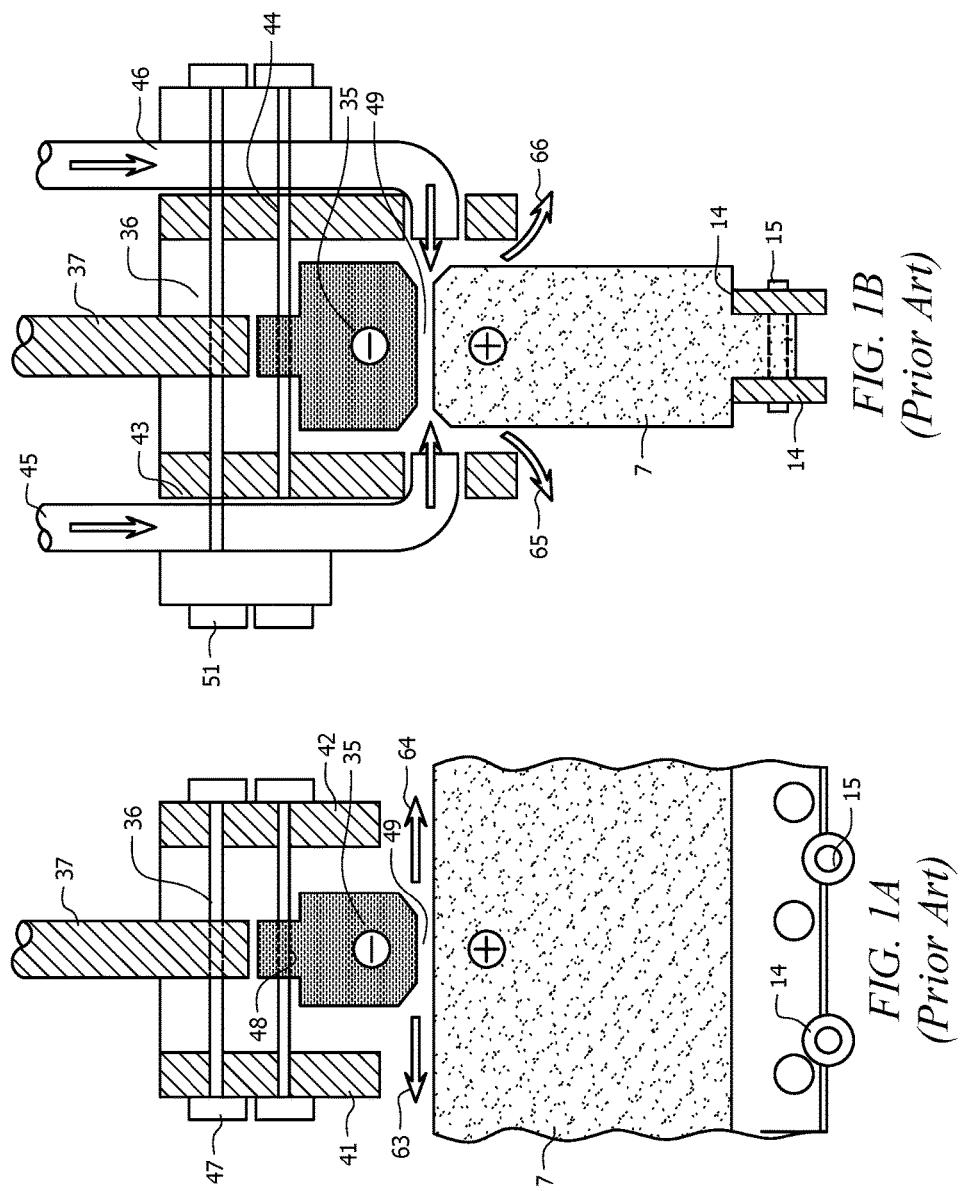
FIG. 1A illustrates a schematic view of a system of the prior art.
FIG. 1B illustrates a schematic view of a system of the prior art.

Reference will now be made in detail to the presently preferred embodiments of the invention, examples of which are illustrated in the accompanying drawings. Throughout the following detailed description, the same reference numerals refer to the same elements in all figures.

Throughout this description, the term liquid (feedstock) refers to a material in liquid state that is to be processed. It is fully anticipated that there are, for some liquids (feedstock), suspended solid materials in the liquid (feedstock). For example, it is anticipated that there are suspended particles of metal in a liquid (feedstock) such as used motor oil.

There are several circulation systems described for flowing the liquid (feedstock) through an arc any number of passes from a single pass, several passes or continually, depending upon the desired result (e.g., sterilize the liquid, produce a clean, burnable gas, etc). There are many different circulation systems known using pumps, check valves, manual valves, electrically controlled valves, solid tubing/pipes, flexible tubing, etc. The specific circulation and flow systems described are examples and other circulation and flow systems are anticipated for the described recycler, including fixed-purpose flow systems, an example of one is a flow system in which there is no circulation, just one pass from the source, through the arc and to the destination.

FIG. 1A show a front sectional view and 1B show a side sectional view of the submerged electrodes 7/35 of the prior art. The liquid (e.g. waste) flows through feed tubes 45/46 toward the plasma of the arc that is formed between the cathode 7 and the anode 35; through the gaps 63/64. The liquid exits from the arc around insulating members 44/42/43/44/36/47/51 to improve the controlled flow of the liquid through the arc as quickly as possible to reduce ignition of produced gasses, thereby increasing the efficiency of gas production.

In this example of the prior art, the cathode 7 is movable horizontally by way of wheels 14/15 and an actuation mechanism (not shown). The anode 35 is movable toward/away with respect to the cathode 7 by a shaft 37 and another actuation mechanism (not shown).

In this example of the prior art, the gap 49 between the cathode 7 and the anode 35 is generally small, for instance, on the order of 2-3 mm for an arc powered by a 50 KW power source and 6-7 mm for an arc powered by a 100 KW power source. Gas is produced by the arc within this gap and violently exits the same. Consequently, only a small part of the liquid (feedstock) flows through the gap 49, estimated to be of about 20% of the total flow of the liquid. The remaining part of the liquid, estimated to be 80%, bounces off the sides of the cathode 7 and anode 35, thus remaining unprocessed.

In some uses of such a recycler, it is required that all or a substantial percentage of the liquid pass through the arc at least once, for example, to neutralize biological agents living in the liquid. Since only an estimated 20% of the liquid passes through the arc of the prior art, the liquid needs to be circulated many times to approach 100%.

The present apparatus and method improves on the prior art by flowing the liquid (feedstock) at a pressure through one or more bores in one or both of the electrodes and directly into the plasma formed by the arc. In this way, the liquid is forced to pass through the gap between the electrodes by the pressure and 100% of the liquid (feedstock) is forced to pass through the electrode gap and exit the gap along with the produced gas. This process increases the efficiency and utility of gas production for a given power input and improves the sterilization of the liquid (feedstock) when infected with biological hazards (e.g. city, farm, ship or other sewage).

Microwave ovens can quickly bring liquids to their boiling temperature via the use of certain frequency radio waves having a frequency that is a sub-multiple, also called sub-harmonic, of one of the resonating frequencies of the liquid itself (e.g., for water, 2.45 GHz). In some embodiments disclosed, the volume of gas produced is increased by the use of similar resonating effects. The volume of gas produced is increased by the use of an "alternating current" (AC) or pulsed DC current that has a frequency that is also a sub-multiple of one of the resonating frequencies of the molecules of the liquid. As such, the liquid (feedstock) is separated by a combination of electron flows as well as disintegrating resonating effects under the resonating frequency.

Yet another feature of this invention is the production of green electricity, namely, electricity meeting the environmental specifications of the Kyoto Accord, including the electricity needed for the arc. Carbon combustion, whether from coal or petroleum, is the biggest esoenergetic combustion industrially available, essentially due to the synthesis of CO that releases about 288 Kcal/mole. The primary source of energy in the Recycler is given by various esoenergetic chemical reactions occurring in the plasma surrounding the arc whose total value has been computed as achieving about fifty times the energy used by the electric arc. Experiments show that the same synthesis of CO with the release of 288 Kcal/mole as occurring in conventional carbon combustion in air but, additionally, the synthesis of H2 yields the release of additional 110 Kcal/mole, the synthesis of CO2 yields 87 Kcal/mole and numerous other esoenergetic reactions as verified by numerous chemical and mass spectrometric analyses. Consequently, green production of electricity occurs in addition to that needed for the operation of the arc, resulting in an efficient, industrially available production of electricity from the produced gas and sterilization of the liquid (feedstock).

Note that the carbon combustion occurs in the Recycler even when recycling water based liquid waste because the needed carbon is supplied by the electrodes. Even though the arc is submerged, the carbon combustion occurs in the plasma surrounding the arc at a temperature much higher than that of conventional carbon combustion in air. Typical fossil fuel operated electric power plants produce electricity solely by carbon combustion. Consequently, the Recycler has a net production of energy because, in addition to the same carbon combustion as in the fossil fuel electric plant, there are additional energy sources such as the synthesis of H2, that are completely absent in the fossil fuel electric plants. Finally, unlike the case of the latter, the net electric energy produced by the Recycler is environmentally clean because the Recycler produces a clean burning Gas and the liquid (feedstock) is rendered sterile with a small percentage of inert solids suitable for industrial uses, without any gasses or liquids released in the environment. In particular, the gas is environmentally clean because it is produced underwater. Its contaminants are the trapped in the liquid (feedstock) while gas bubbles travel to the surface where they are captured and contaminants are then decomposed by the arc and recycled back to gas, sterile liquid and a small amount of solid residue.

As a numerical illustration with a small power and low operating pressure, the above indicated Recycler operated at the pressure of 30 pounds per square inch (psi) and was powered by 50 KW AC-DC converter; consuming a total of about 55 KWh including the pumps corresponding to about 180,000 British Thermal Units per hour (BTU/h) in electricity. The Recycler produced about 500 SCF of gas per hour corresponding to about 500,000 BTU/h, plus about 500,000 BTU/h of heat acquired by the liquid (feedstock). Consequently, in this Recycler operated at the indicated power and pressure, the indicated esoenergetic reactions in the arc plasma produce about 5.5 units of energy per each unit of electric energy used. Consequently, the use of Gas as fuel for recent CO-tolerant fuel cells with about 90% efficiency would produce 450,000 BTU/h of electricity, plus the conversion of heat to electricity with one of the industrially available means with 20% efficiency would produce 100,000 BTU/h for a total of 600,000 BTU/h corresponding to about 190 KWh, namely, 105 KWh more than the used electricity.

The above example deals with a small Reactor operated at low pressure. Industrial production of electricity requires the use of industrial Recyclers with at least 300 KW of AC power at high resonating frequency operated at least at 3,000 psi so as to avoid the use of the expensive compression of gas for its storage and use as well as to enhance the production of a safe liquid. Measurements of the Recycler have established the production of about 10,000 SCF/h of Gas, since the efficiency in gas production increases with the increase of the power due to a proportionate increase of the gap and a large increase of produced gas due to the resonating effect, which corresponds to about 10 million BTU/h. The produced heat increases exponentially with the increase of the pressure as well as increases nonlinearly with the increase of the power, with gas production using 300 KW of high frequency AC power operated at 3,000 psi pressure of about 100 millions BTU/h for a total of about 110 millions BTU/h corresponding to the use of about 1.5 million BTU of electricity. In this case, the combustion of the gas, the combination of the resulting heat with the heat acquired by the liquid (feedstock), and the use of a turbine to convert the heat into electricity at 20% efficiency would yield about 22 millions of BTU/h corresponding to 7,000 KWh, namely, about 6.700 KWh more than the used electricity.

The energy of the output, whether referring to the energy in the produced combustible gas or to the energy of the produced heat or both, is increased significantly by several factors. A first factor is the use of a DC current with high voltage, such as 100,000 V, DC current. Another factor is the use of a high voltage DC current pulsating at a resonating frequency or sub-multiple of the resonating frequency of the processed liquid (feedstock). Another factor is forcing the liquid (feedstock) through the arc to reduce collection of gas bubbles within the arc that lead to unwanted ignition of the gas bubbles and/or the arc passing through the higher impedance gas bubbles rather than the lower impedance liquid (feedstock).

As the combustible gas is produced within the arc, some of the gas is ignited by the arc, forming pressure waves.

Figure 2:
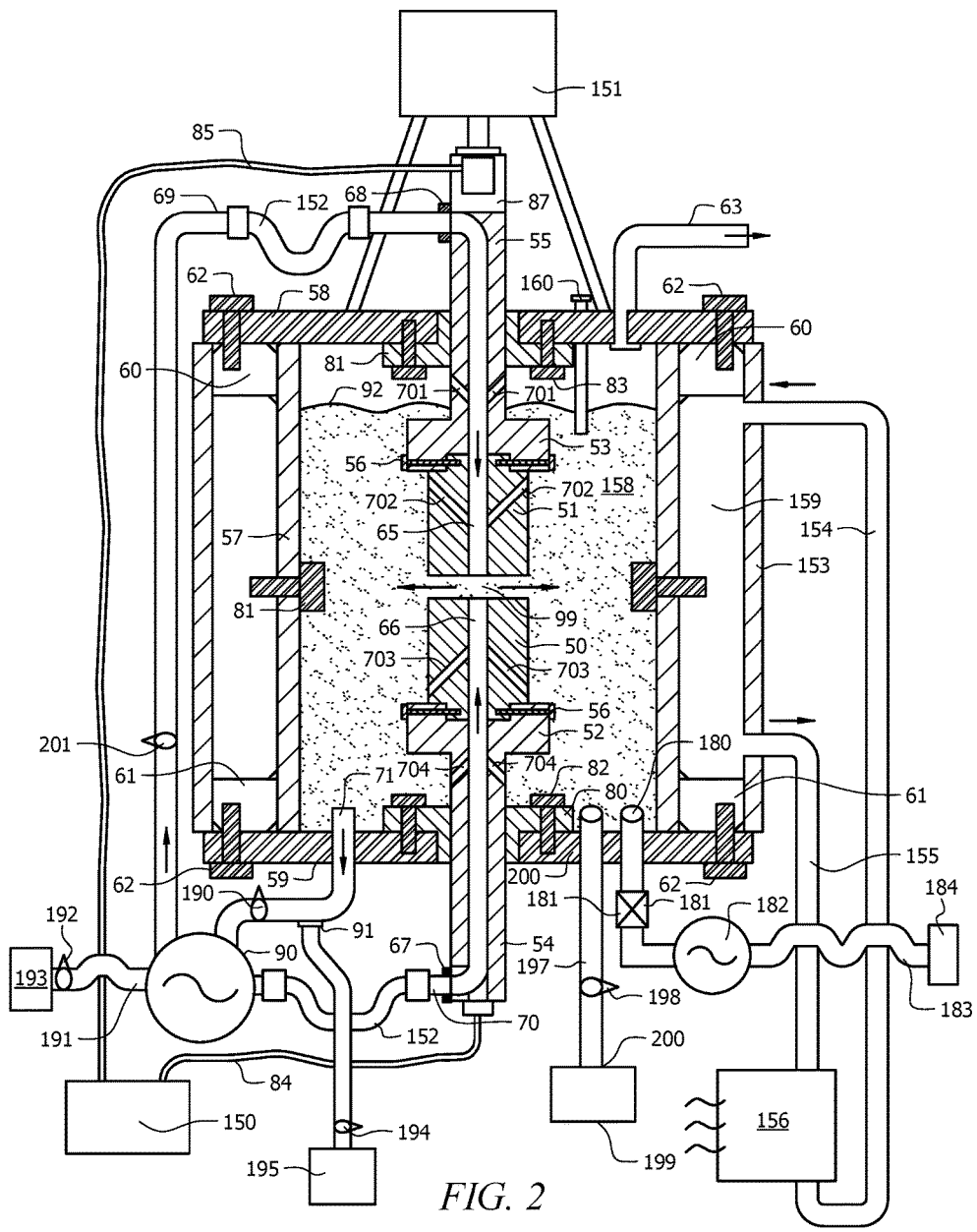
FIG. 2 illustrates a schematic view of a recycler system of a first embodiment.

Referring to FIG. 2, an exemplary system for recycling of a liquid (feedstock) and producing a combustible gas is shown. It is anticipated that, the liquid (feedstock) is, for example, a highly contaminated municipal, farm, industrial, military and other liquid waste such as used motor oil. As stated above, it is anticipated that some solids are also present in the liquid such as vegetable seeds, sand, etc. in waste; or metal fragments in the used motor oil.

The exemplary recycler of FIG. 2 comprises a case 57 made of, for example, standard, schedule, carbon steel pipe with 24 inches outside diameter and 5 feet in length. Hollow flanges 60/61, are welded to the case 57 at each extremity via welding procedures that assure operation at the operating pressure (e.g. 300 psi). Two plain flanges 58/59 (e.g. standard, schedule carbon steel flanges) are fastened to hollow flanges 60/61, with bolts 62 or other fastener sealing the ends of the outer case 57 and assuring safe operation at standard operating pressure.

Electrodes 50/51 housed in the interior of the outer case 57. The electrodes 50/51 are preferably made of the standard graphite composition, such as commercially available for arc furnaces. In some embodiments, the electrodes 50/51 have a dimension of approximately 6 inches in outside diameter and 24 inches in length. The electrodes 50/51 are retained by conducting metal holders 52/53 and locked to the holders 52/53 by fasteners 56. The conducting metal holders 52/53 connect or continue into conducting metal shafts 54/55. The shafts 54/55 pass through the plain flanges 58/59, insulated by bushings 80/81. In some embodiments, the insulating bushings 80/81 are made of phenolic or an equivalent insulating, temperature and pressure resistant material. In one embodiment, the conducting metal shafts 54/55 have an outside diameter of 3 inches and a length of 2 feet. The insulating bushings 80/81 are fastened to the flanges 58/59 by bolts 82/83 (or equivalent commercially available attachment devices).

At least one or both of conducting metal shafts 54/55 are disposed to move along their axial symmetry; said conducting metal shafts 54/55 being connected via cables 84/85 to an electric power source 150. For example, the axial displacement of conducting metal shaft 55 is performed by an actuator 151 (e.g., an actuator or other similar device). The actuator 151 initiates, maintains and optimizes the submerged electric arc in the gap 99 between the electrodes 50/51. Axial displacement of conducting metal shaft 55 is allowed by flexible cables 84/85 and flexible feed hoses 152. The feed hoses 152 and related flanges 67/68 are fed with the liquid (feedstock) by a pump 90.

In a preferred embodiment, the electric power source 150 consists of either an AC to DC converter or a two phases AC power source. In some embodiments, the electric power source 150 has a variable output voltage (e.g. up to 1,000V) and/or a variable output frequency (e.g. 0 to 10,000 Hz).

The level 92 of the liquid 158 is monitored by a sensor/probe 160 or other device for monitoring level 92 of the liquid (feedstock) 158 within the case 57.

In some embodiments, an outer case 153 (e.g. another Schedule 80 carbon steel pipe of greater diameter than the case 57) is welded to the hollow flanges 60/61 so as also to withstand the operating pressure (e.g. a pressure of 300 psi). The volume between the case 57 and outer case 153 is filled with a heat transfer liquid 159 suitable for the recovery of the heat produced in the interior of the vessel. At least one input port and related pipe 154 provides for the flow of the heat transfer liquid 159 into the volume between the case 57 and outer case 153 and at least one exit port and related pipe 155 provides for the exit of the heat transfer liquid 159. The pipes 154 and 155 are connected to a heat recovery device 156 such as a turbine run electric generator 156 or other industrially available device for the production of electric current. Electric current is generated in any way known through the use of heat absorbed by the heat transfer liquid 159 when the heat transfer liquid is between the case 57 and outer case 153. For example, the heat is used to generate steam and the steam turns a turbine that is interfaced to an electric generator or the heat is converted to electricity by a fuel cell, etc.

In some modes of operation, the liquid (feedstock) 158 enters through a pipe 180 that passes through the flange 59 and through check valve 181 from a pump 182, from another pipe 183 to from a tank 184 that contains the liquid waste to be recycled. The Recycler is automatically refilled from the source tank 184 under electronic control whenever sensor 160 detects the decrease of the level 92 of the liquid waste 158 below the allowed value by the pump 90.

In some modes of operation, the liquid (feedstock) 158 from, for example, a sewerage system 193, enters through a pipe 191 through a valve 192 directly into the circulation pump 90. This enables, for example, a one-pass routing of the liquid (feedstock 158) from the sewerage system 193, through the pump 90, through the arc/gap 99 and out one of the exits 180/200.

After processing, the liquid (feedstock) flows out through an opening 200 in the flange 59 through a pipe 197 under control of an exit valve 198 into, for example, a storage tank 199.

The electrodes 50/51 include bores 65/66 (e.g. about one inch in diameter machined or formed along the axis of electrodes 50/51). The bores 65/66, continue along the axial symmetry of conducting metal holders 52/53 and conducting metal shafts 54/55 and connect exterior of the apparatus to circulation input pipes 69/70 by fittings 67/68. In some embodiments, the circulation pipes 69/70 are 1 inch diameter standard steel pipes. The circulation input pipes 69/70 are connected to a circulation pump 90 that continually circulates the liquid (feedstock) 158 through the bores 65/66 and into the gap 99.

As, for example, some of the produced combustible gases are ignited by the arc between the electrodes 50/51, back pressure waves occur, pushing the feedstock 158 in a reverse direction into the bores 65/66 and causing, for example, foaming of certain feedstock 158. This disrupts the flow of feedstock 158 and reduces efficiency. In some embodiments, to reduce, for example, the back pressure caused by the combustion of the combustible gases, one or more vents 702/703 are drilled or formed in the electrodes 50/51, one or more vents 701/704 are drilled or formed in the metal holders 52/53, or in both the electrodes 50/51 and the metal holders 52/53. The vents 701/702/703/704 are drilled or formed at an angle with respect to the axis of the electrodes 50/51 and/or the metal holders 52/53, reducing parasitic outflow while facilitating escape of feedstock 158 that reverses flow under, for example, back flash pressure. Although there is no restriction on the angle, it is preferred that the vents 701/702/703/704 angle towards the flow of feedstock 158 within the electrodes 50/51 and/or the metal holders 52/53. In other words, the preferred angle of the vent(s) is such that, during the normal flow of the feedstock through the electrodes 50/51 and the metal holders 52/53, little feedstock 158 exits the vents 701/702/703/704 or, for some angles, feedstock 158 is drawn in through the vents 701/702/703/704. When back flow occurs (e.g. due to combustion or micro-explosions of the combustible gases), forces temporary reverses the flow of the feedstock 158 (e.g., back into the electrodes 50/51). Since the vents 701/702/703/704 are preferably angled towards the gap 99 (e.g. location of the arc), feedstock 158 flowing in this reverse direction exits the vents 701/702/703/704, reducing the back flash pressure.

Any number of vents 701/702/703/704 is anticipated, including one vent 701/702/703/704.

The apparatus is further equipped with a circulation drain 71 to exit the liquid (feedstock) 158 through an exit pipe 91 (e.g. 2 inches diameter standard steel pipe) to the pump 90 for continued recirculation under control of a valve 190.

A gas collection pipe 63 is connected to the top plain flange 58 releasing the produced gas for collection and use. The collected gas is contained and/or compressed in ways known in the industry.

The operation of this embodiment is described. There are at least three modes of operation depending upon the type of liquid (feedstock) being processed: Total, Total Linear and Linear. Total is a mode in which the liquid from the feedstock must be completely eliminated. This class of liquid (feedstock) is typically oil based liquid wastes such as used engine oil, used cooking oil, oil contaminated by salt water, etc. Total Linear is typical for sewerage and Linear is typical for contaminated water such as in the production of reclaimed water.

Total Linear is used for a liquid (feedstock) that has a significant amount of biological contaminates (e.g., 10%), in which the liquid (feedstock) is circulated several times through the arc to neutralize contaminates. Examples of such liquid (feedstock) includes infectious city sludge, farm sludge, ship sludge, military sludge, industrial sludge, etc, having up to 10% biological contaminants. The biological contaminants are generally referred to as Total Suspended Solids (TSS).

Linear is used for a liquid (feedstock) that has some biological contaminates (e.g. 1%), for example city sewage, farm sewage, ship sewage, military sewage, industrial sewage and other liquids that have, for example, up to 1% of infections contaminants (TSS). In this mode, the liquid (feedstock) passes through the arc only once.

The liquid (feedstock) is examined to ascertain whether it must be entirely reduced (e.g. little or no liquid and only a small amount of solid residue remains) or whether it can be successfully recycled at least in part into usable liquids such as reclaimed water.

The liquid (feedstock or waste) starts in the source tank 184. In Total Mode, the liquid must be entirely eliminated. The liquid (feedstock) is continuously circulated through the arc and generates a clean burning gas that is released through port 63. During the process, heat is captured and utilized by the heat recovery system 156 and a small percentage of inert solid residues are deposited at the bottom of the apparatus for periodical collection.

In Total Mode, the liquid (feedstock) is pumped from tank 184 into the apparatus to the fill level 92. Additional liquid (feedstock) is pumped from the source tank 184 into the apparatus when the level sensor 160 determines that the liquid (feedstock) level falls below the fill level 92. In Total Mode, the input valve 192 and the output valve 198 are closed and the circulation valves 190/201 are open. The pump 90 continuously circulates the liquid 158 through the electric arc in the gap 99 between electrodes 50/51. The liquid and the produced gas exit the gap 99, avoiding ignition/recombination of the gas caused by the arc/plasma. This operation and internal pressure produces a large amount of heat that is converted into electricity by the heat recovery system 156. Additional energy is recovered by combustion of the produced gas.

In Total-Linear, it is not economically advantageous to eliminate all of the liquid. The goal is to neutralize all or most of the biological contaminants (a portion of the liquid is biological contaminants, e.g. 10%). In Total-Linear mode, the circulation valves 190/201 and the input valve 192 are open and the output valve 198 is closed. In this case, the liquid waste is continuously pumped into the apparatus from the input tank 184 by the pump 182. The pump 182 operates at a moderate rate, pumping a moderate number of gallons per minutes (e.g., at 20 gpm corresponding to 1,200 gallons per hour) while the circulation pump 90 is operated at maximal flow (e.g., 100 gpm) producing maximum arc stability. The sterilized liquid waste exits through the exit tube 197 to the external tank 199 while the produced gas is expelled at a controlled pressure through the port 63. The liquid waste flows through the arc several times before being expelled to the external tank 199. For instance, using an example value of 20 gpm for inlet pump 182 and 100 gpm for the circulation pump 90, the liquid waste flows through the arc five times before being expelled to the external tank 199, thus allowing the sterilization of highly infective liquids. The flow of the liquid through the gap 99 of the electrodes along with the produced gas increases the efficiency and utility.

In Linear mode, the liquid waste is passed through the arc one time, sufficient for sterilization, and then the sterilized liquid waste is released to the outside of the apparatus. For example, the released, sterilized liquid waste is treated by conventional water deputation equipment as known to those skilled in the art. In Linear mode, the circulation valves 190/201, the input valve 192 and the output valve 198 are open. Sewage from the source tank 193 is pumped through the arc by the circulation pump 90. A sterilized form of the liquid exits through the output port 200 to the output tank 199 by way of pressure of the gas inside the vessel (e.g. without any need of pumps). The output valve 198 is adjusted to maintain the correct level 92 of the liquid (feedstock) for the selected flow of incoming liquid (feedstock). Again, the entirety of the liquid (feedstock) is passed through the arc along with the creation of the gas, thus improving efficiency and utility.

The power source 150 is, for example, an AC-DC welder; a high voltage DC current source; a pulsed DC current source, pulsating at a frequency which is a sub-multiple of a resonating frequency of the selected liquid; an AC welder; an AC source with variable high voltage and high frequency; an AC source with variable frequency which is a sub-multiple of the resonating frequency of the selected liquid; or other commercially available sources of electricity suitable to create a submerged electric arc.

For the sterilization of highly biologically contaminated liquid (feedstock), the use of the DC welder is preferred. When the goal is production of the gas, the Pulsating DC sources or high frequency AC sources are recommended. The latter sources are preferred to have variable frequencies because different liquid wastes have different resonating frequencies. In some cases, the voltage and/or frequency is varied until achieving a maximum production of the gas.

Figure 3:
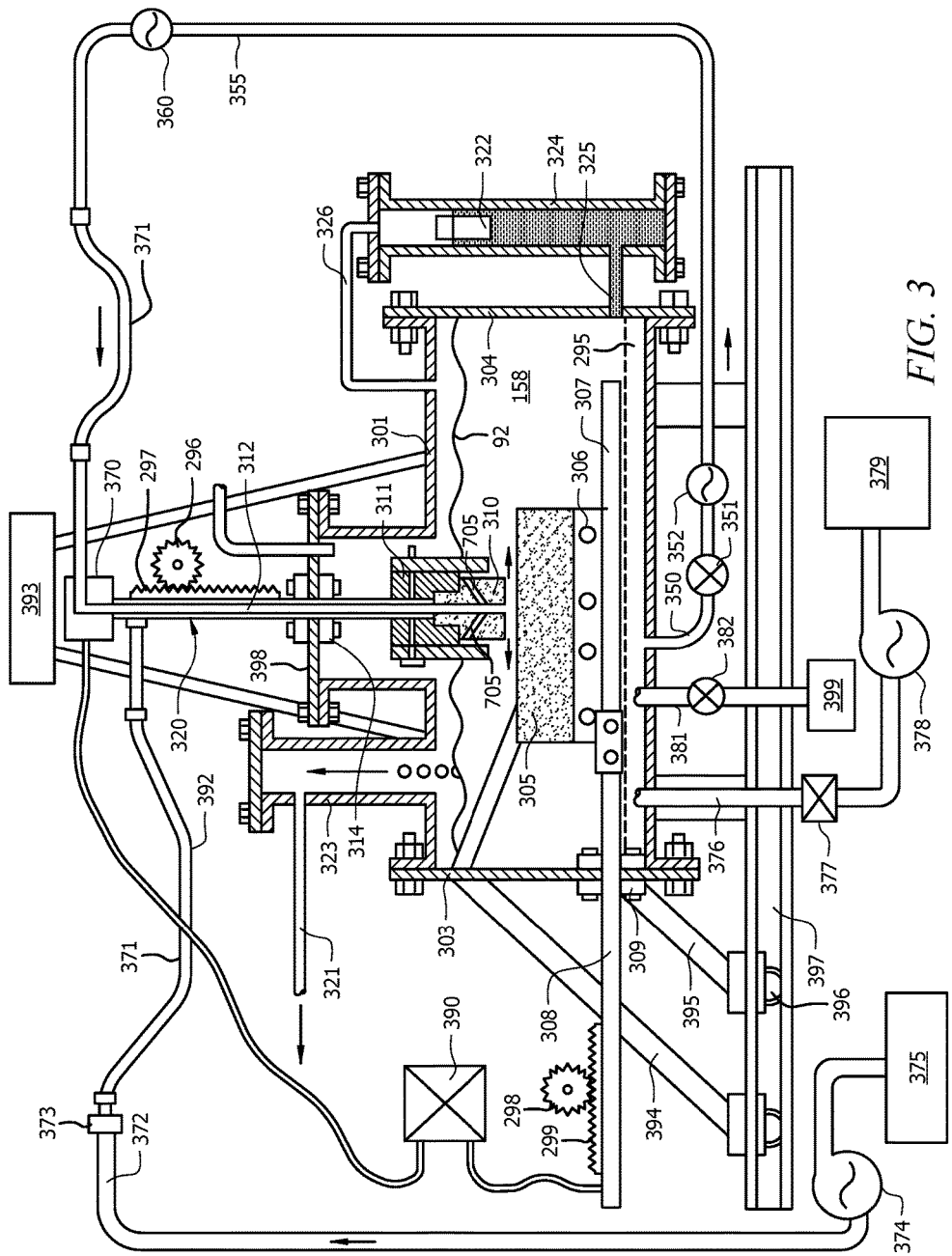
FIG. 3 illustrates a schematic view of a recycler system of a second embodiment.

A second embodiment is shown in FIG. 3. This recycler includes a vessel 301 (e.g., a horizontal Schedule 80 carbon steel pipe two feet in outer diameter and seven feet long) completed by end caps 303/304; a horizontal electrode 305 (e.g. carbon electrodes 305) (e.g. 5" width, 10" height and 3 ft length) held by a pair of conducting metal bars 306, one on each side of the electrode 305. The metal bars 306 are housed in a sled 307 that is electrically insulated from the vessel 301. The sled 307 moves to the right and left within vessel 301, for example, on railings 295. The metal bars 306 are electrically and mechanically connected to a conductive metal shaft 308 (e.g. 3 inches in diameter) that passes through the end cap 303 through electrically insulated seals 309. It is preferred, though not required, that the shaft 308 is long enough as to allow the entire travel of sled 307 from one end to the opposite end of the interior of the vessel 301. Such horizontal motion is performed by an actuator (e.g. motor gear 298 and a gear rack 299 that is coupled to the shaft 308). The actuator moves the electrode 305 vertically (e.g. at a speed of about ½ inch per minute). A second, vertically placed electrode 310 (e.g. carbon electrode 310) is held by conducting metal fastener 311 that is electrically connected and fastened to a conducting metal shaft 320 that extends through an upper plate 398 of the vessel 301 through an electrically insulating bushing 314. The shaft 320 is long enough (e.g. at least 3 ft long) to provide vertical motion upward and downward of electrode 310 toward/away from electrode 305. In one embodiment, the electrode 310 is 5 inches wide, 10 inches long and 1 foot height. The assembly consisting of electrode 310, holder 311 and shaft 320 has an inner bore 312 running the length of the shaft 320 and electrode 310. The shaft 320 and electrode 310 are moved or adjusted vertically by an actuator (e.g. motor gear 296 and a gear rack 297, the later being coupled to the shaft 320).

The vessel 301 is filled with the liquid (feedstock) 158 to be recycled up to level 92. A gas collector 323 protrudes upward from the vessel 301 and ends with exit pipe 321. In some embodiments, the vessel 301 is interfaced to a tower 324. The tower measures the level 92 of the liquid (feedstock) 158 by a float 322. Liquid flows to/from the vessel 301 through a tube 325 into the tower 324 and pressure is equalized between the tower 324 and the vessel 301 by a second tube 326. In one embodiment, the tower is made of a schedule 80 pipe 1 foot OD and 3 feet high completed with schedule 80 welded-on hollow flanges and bolted-on plain flanges. In other embodiments, other level sensors are anticipated as known in the industry.

The vessel 301 is filled with the liquid (feedstock) 158 by a fill pipe 376 through a one-directional check valve 377 from a source tank 379 by a fill pump 378. The liquid (feedstock) 158 is circulated through the arc between the electrodes 305 and 310. During circulation, the liquid is pumped from the vessel 301 by a circulation pump 352 from an exit pipe 350, through an exit valve 351. The liquid 158 flows through a circulation pipe 355, through a circulation check valve 360 and flexible hose 371 and into a fitting 370, delivering the circulated liquid flow into the bore 312 in the interior of shaft 320.

In some embodiments, the vessel 301 is equipped with a waste pipe 381 and waste valve 382 connected to a waste tank 399. After processing, remaining materials are removed from the vessel through the waste pipe 381 and waste valve 382.

The electrodes are electrically connected to a power source 390 by cables 391/392. The power source 390 is, for example, two 100 KW power units, the first consisting of an AC-DC converter and the second consisting of an AC power source with variable voltage up to 600 V and variable frequency up to 10,000 Hz. One polarity of the power source 390 is connected by cable 392 to conducting metal shaft 308 and the other polarity of the power source 390 is connected by cable 391 to conducting metal shaft 320. An electronic control 393 electrically connected to all valves 377/351/373, all pumps 374/378/351 and all sensors 322 for control of their operation. The control 393 initiates the electric arc by, for example, a short between electrodes 305 and 310, as necessary for a submerged electric arc, then maintains the arc by micro-metric motions upward or downward of shaft 320, optimizing the arc by increasing the gap while maintaining a stable arc with a pre-determined variation of the voltage.

In some embodiments, the end cap 303 is welded to supports 394/395 that are connected to wheels 396 operating in railings 397. This provides a mechanism for the removal of the entire internal assembly of electrode 305 and supports for fast and easy replacement of the electrode 305.

In some embodiments, the vessel 301 is equipped with a heat recovery system 156 as in the embodiment of FIG. 2. This is not reproduced in FIG. 3 to avoid unnecessary repetition and clutter. The heat recovery system 156 (not shown in FIG. 3) comprises a metal chamber surrounding the outside of vessel 301 through which a coolant is passes and connected to an external system for the production of electricity from the generated heat.

In the Total Mode of operation, the vessel 301 is filled up with the liquid (feedstock) to be recycled from the source tank 379 by the fill pump 378, feeding the liquid (feedstock) through pipe 376 and check valve 377 into the vessel 301 until the level 92 is reached. The liquid (feedstock) is precluded from returning to tank 379 by the one directional check valve 377. Whenever the liquid is consumed by the recycler below a pre-determined level, the fill pump 378 is re-activated by controls 393 to again reach the desired level 92. The level 92 is checked by, for example, the tower 324 or any suitable level sensing device/system.

Before starting operation, in some embodiments, the vessel 301 is purged with gas or an inert gas. The feed valve 373 is closed and the arc is activated between electrodes 305/310. The circulation pump 352 runs to circulate the liquid (feedstock) 158 from the vessel 302, through the recirculation pipes/tubes 355/371, through the bore 312 and into the arc between the electrodes 310/305. The liquid (feedstock) 158 is converted into the clean burning gas that percolates up and is collected in the collector 323 and exits the system through a gas pipe 321 for use or storage. The liquid (feedstock) acquires heat and a small percentage of inert gas. Sterilized solids precipitate at the bottom of vessel 301 for periodical collection.

In the Total-Linear mode of operation, circulation of the liquid (feedstock) 158 through the arc is performed while the feed valve 373 is closed. The exit valve 382 is open by automatic controls 393 for an amount permitting the maintenance of the liquid level 92 for a given incoming flow from the source tank 379 by the source pump 377 through the check valve 377 and pipe 376. The sterilized liquid (feedstock) 158 is released into outside tank 399 for processing into usable byproducts via the use of commercially available equipment (not shown).

In the Linear Mode of operation vessel 301, the feed valve 373 and the waste valve 382 are open while the circulation valve is closed. The liquid (feedstock) 158 is pumped from an external input/tank 375 by a feed pump 374, through a feed valve 373, through a fill pipe 372, through a flexible hose 371 and into the fitting 370 for delivery of the liquid (feedstock) into the bore 312 of the shaft 320. The flexible hose 371 delivers the liquid (feedstock) 158 to the fitting 370 while shaft 320 moves up or down. The liquid (feedstock) 158 flows through the gap between the electrodes 310/305 and is exposed to the high temperatures of the arc, very strong ultra violet rays and other agents that impact sterilization. The sterilized liquid (feedstock) 158 is them released through the exit pipe 381 and open exit valve 382 into external tank 399.

As some of the produced combustible gases are ignited by the arc between the electrodes 305/310, back pressure waves occur, pushing the feedstock 158 in a reverse direction into the bore 312. This disrupts the flow of feedstock 158 and reduces efficiency. In some embodiments, to reduce the back pressure caused by the combustion of the combustible gases, one or more back 705 are drilled or formed in the electrode 310, one or more vents are drilled or formed in the metal holder 311 (not shown for clarity reasons), or in both the electrode 310 and the metal holder 311. The vents 705 are drilled or formed at an angle with respect to the axis of the electrode 310 and/or the metal holder 311, reducing parasitic outflow while facilitating escape of feedstock 158 that reverses flow under back flash pressure. Although there is no restriction on the angle, it is preferred that the vents 705 angle towards the flow of feedstock 158 within the electrode 310 and/or the metal holder 311. In other words, the angle is such that, during the normal flow of the feedstock through the electrode 310 and the metal holder 311, little feedstock 158 exits the vents 705 or, for some angles, feedstock 158 is drawn in through the vents 705. When back flow occurs (e.g. due to combustion or micro-explosions of the combustible gases), forces temporary reverses the flow of the feedstock 158 (e.g., back into the electrode 310). Since the vents 705 are preferably angled towards the gap between the electrodes 305/310 (e.g. location of the arc), feedstock 158 flowing in this reverse direction exits the vents 705, reducing the back flash pressure.

Any number of vents 705 is anticipated, including one vent.

Figure 4:
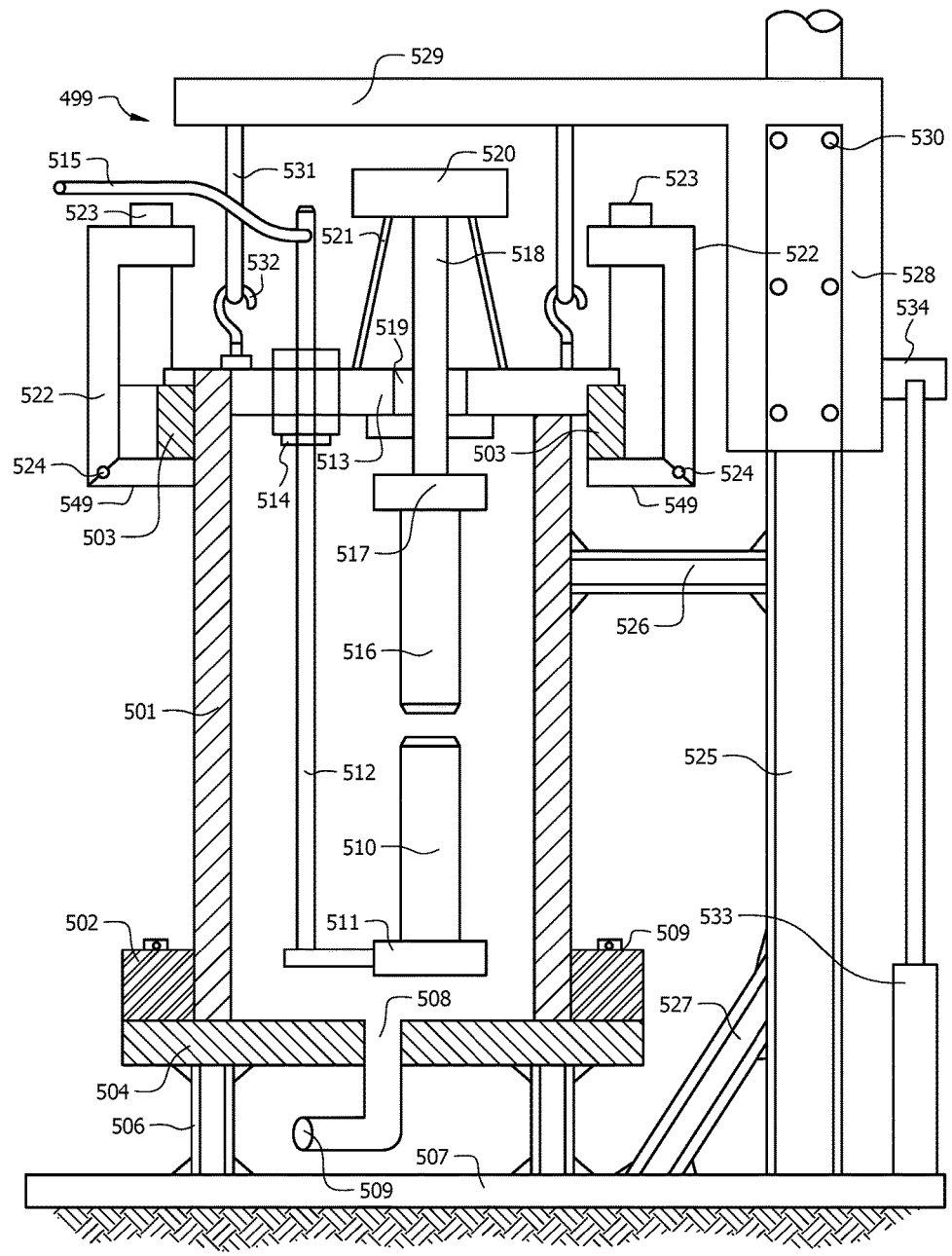
FIG. 4 illustrates a schematic view of a recycler system of a third embodiment.

FIG. 4 depicts another embodiment of the recycler. The circulation control system is not described for brevity purposes. This recycler 499 includes metal walls 501 (e.g. made of five foot tall and 24 inch wide schedule 80 steel pipe) with hollow flanges 502/503 welded at each end. A plain flange 504 (e.g. schedule 80) is permanently fastened to the lower hollow flange 502 by, for example bolts 505. The plain flange 504 is welded to supports 506 that are, in turn welded to a metal basement 507 encompassing the entire floor area of the equipment. The plan flange 504 has one or more holes connected to a pipe 509 and valves (not shown) for operating in modes previously described. A lower electrode 510 is held by conducting metal holder 511 and connected to a conducting metal rod 512 (e.g. 3 inch metal rod) that protrudes through the top plain flange 513 through an insulating bushing 514 with fasteners so as to prevent the upward or downward motion of rod 512. A first electric power cable 515 from a power source (not shown, see previous figures) is connected to the rod 512. An upper electrode 516 is held by conducting metal holder 517 and connected to a conducting metal rod 518 (e.g. 3 inch metal rod) that protrudes through the top plain flange 513 through an insulating bushing 519 allowing upward or downward motion of rod 518. A second electric power cable from a power source (not shown, see previous figures) is connected to the rod 518. The upper end of the rod 518 is connected to an actuator 520 fastened to flange 513 by metal support legs 521. The actuator 520 moves the upper rod 518 and, therefore, the upper electrode 516 closer or farther from the lower electrode 510 to start the arc and then to control the arc between electrodes 510 and 516. The gap is maximized by moving the electrode 516 upward to reach the maximum stable arc for a preset variation of voltage.

In some embodiments, the plain flange 513 is held to the metal walls 501 at pressure by two or more hydraulic pistons 523 applying pressure against the hollow flange 503 by two or more hydraulic clamps 522 having a lower part 549 welded to the hollow flange 503 and equipped with hinges 524. The upper portion of clamp 522 and related hydraulic piston 523 is rotated away to leave plain flange 513 free to be removed upwardly.

In some embodiments, the recycler 499 is further equipped with a metal support 525 (e.g. 5" wide 10' tall) that is welded to wall 501 and to basement 507 via supports 526/527. The support 525 has a metal casing 528 that surrounds an upper area of the support 525. The metal casing 528 slides upward or downward along railing 525 on rollers 530. The casing 528 has a metal arm 529 that extends outward, over the plain flange 513 and is fastened to the plain flange 513 by, for example, chains 531 that are connected to hooks 532 or equivalent. The metal casing 528 is further equipped with one or more hydraulic pistons 533. The pistons 533 push upward against a flange 534 (e.g. welded to the casing 528). When the electrodes 510/516 need replacement, power for the arc is disconnected, the hydraulic clamps 532 are released to free the plain flange 513 and the hydraulic piston 533 is activated to lift plain flange 513 until the electrodes 510/516 are exposed for maintenance and/or replacement. After maintenance and/or replacement, the hydraulic piston 533 is operated to lower flange 513 into position against the metal walls 501 and the clamps 522 being locked and the recycler 499 is ready to resume operations.

It is anticipated that the recycler 499 include a similar method, control and apparatus as previously described for flowing the liquid (feedstock 158) through one or both of the electrodes 510/516

Figure 5:
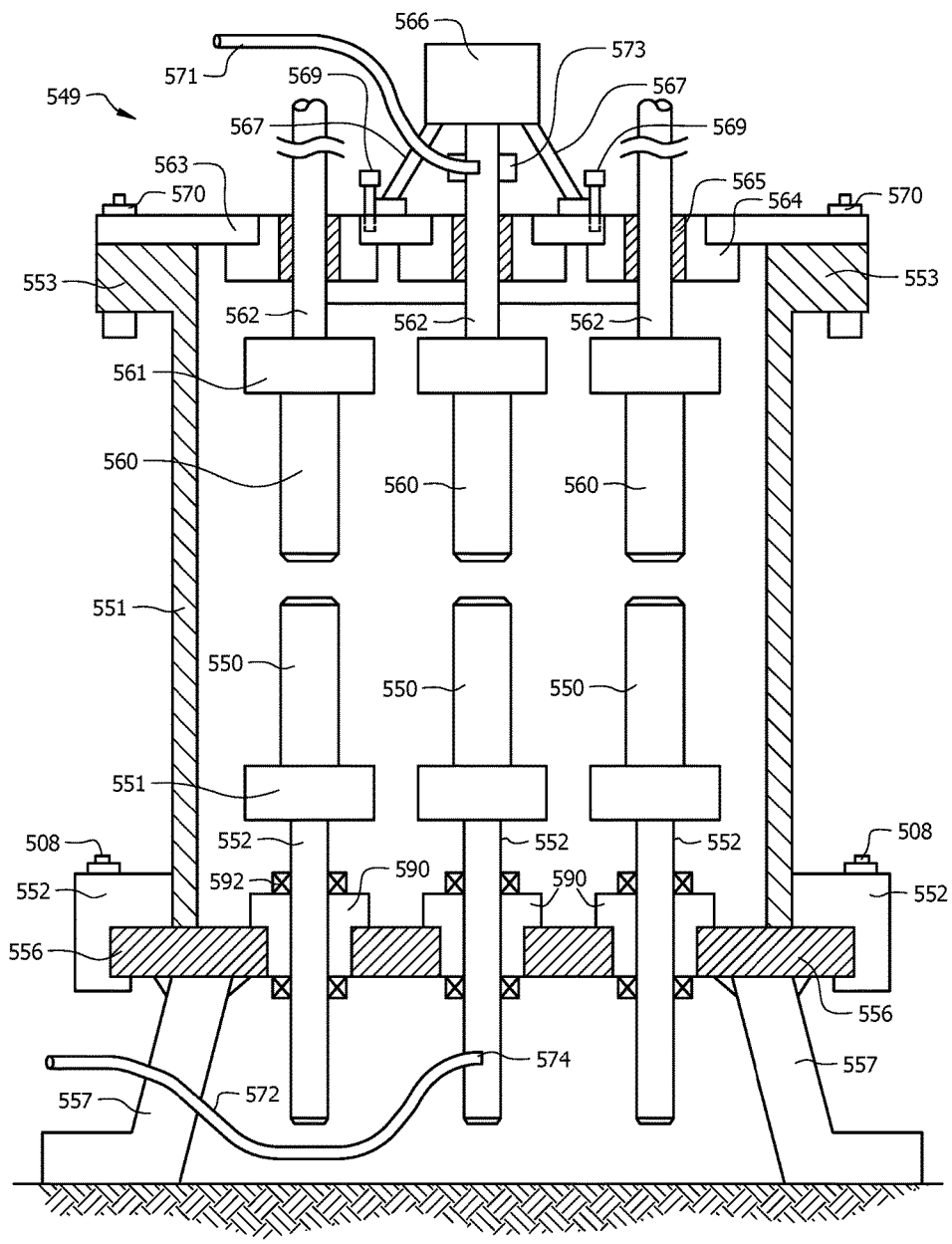
FIG. 5 illustrates a schematic view of a recycler system of a fourth embodiment.

FIG. 5 depicts another embodiment of the recycler 549 designed to achieve greater throughput and a longer operating life of the recycler before maintenance of the electrodes. The circulation control system is not described for brevity purposes.

The recycler 549 has metal edges 552/553 welded to the walls 551 of the vessel 549. The lower part of vessel 549 is completed by a pressure resistant metal plate 556 that is fastened to edges 552 via bolts 508 or similar means. The metal plate 556 is supported by legs 557 to provide clearance between the plate 556 and the ground (e.g. at least one foot clearance). There are three or more lower electrodes 550 (e.g., five inches diameter and three feet long carbon electrodes), each lower electrode 550 is held by a conducting metal holder 551 and each electrode 550 is connected to a lower metal rod 552 (e.g. three inches diameter metal rod). The lower metal rods 552 protrude through the plate 556 and are insulated from the plate 556 by bushings 590 that have collars 592. The rods 552 are fixed in place (do not move up/down). The vessel 549 has three or more upper electrodes 560 (e.g., five inches diameter and three feet long carbon electrodes), each upper electrode 560 is held by a conducting metal holder 561 and each upper electrode 560 is connected to an upper metal rod 562 (e.g. three inches diameter metal rod) that protrudes through the plate 563. The upper metal rods 562 are insulated from the plate 564 by bushings 565. The bushings 565 seal the vessel 549 while enabling upward and downward movement of upper metal rods 562.

A protruding end of one of the upper rods 562 is removably fastened to an actuator 566 (or other movement device) for the automatic control of the arc between upper electrode 550 and the lower electrode 560. The actuator 566 is supported by rods 567 that are affixed to the top plate 563 by removable fasteners 569. The vessel 549 is closed by the top plate 563 fastened to the top edge 553 by, for example, bolts 570.

Electric power is delivered to electrodes 550/560 by power cables 571/572 and electric connectors 573/574, respectively. The electric connectors 573/574 are such that the power cables 571/572 are easily and quickly moved to any of the other rods 552/562 and electrodes 550/560.

In operation, for tuning of the arc and compensation as the electrodes 550/560 erode, the actuator 566 moves the upper electrode 560 closer or farther from the lower electrode 550 to which the actuator 566 is attached. When a first set of electrodes 550/560 are exhausted, the actuator 556 is unbolted from the top plate 563 and detached from the upper shaft 562 corresponding to the first set of electrodes 550/560. The actuator 556 is then transferred to another upper rod 552 of a good set of electrodes 550/560 and reattached/bolted to the top plate 563. The electrical cables 571/572 are then disconnected from the upper rod 562 and lower rod 552 corresponding to the first set of electrodes 550/560 and connected to the upper rod 562 and lower rod 552 corresponding to the good set of electrodes 550/560. In this way, minimal interruption of operation is achieved by quickly transferring operation from one set of electrodes 550/560 to a next set of electrodes 550/560 without disassembling the entire recycler 549.

Operations being essentially the same as those of the embodiment of described above, the main difference being that with the exhaustion of one set of electrodes 550/560, the power and actuator 566 (for the control of the arc) is moved to another set of electrodes 550/560 until all sets of electrodes 550/560 are exhausted, thereby increasing the operating time before maintenance is needed.

Although shown with three electrode pairs 550/560, any number of pairs is anticipated including two pairs. Also, although shown with one actuator 566, in some embodiments, multiple actuators 566 are employed such as one actuator 566 per pair of electrodes 550/560. Although shown as a removable electric connection between the power cables 571/572 and the rods 562/552, it is anticipated that in some embodiments, each rod has an attached cable and the electric power is switched to the pair of electrodes 550/560 by one or more electric switches (not shown).

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An apparatus for producing usable energy comprising:
   a pressure and temperature resistant vessel at least partially filled with a liquid;
   two electrodes held within the vessel and submerged within the liquid, a longitudinal bore passing through a first electrode of the two of electrodes;
   means for delivering an electric current to each of the two electrodes, forming an arc between the two electrodes; the liquid flows through the bore and exits the bore at the arc; and
   at least one vent formed through a side of the first electrode, the at least one vent fluidly interfacing the bore and an area outside of the first electrode within the pressure and temperature resistant vessel;
   wherein a combustible gas is produced by the arc and the combustible gas percolates to the surface of the liquid for collection.

2. The apparatus according to claim 1, wherein at least one of the two electrodes is a carbon-based electrode.

3. The apparatus according to claim 1, wherein the electric current is a direct electric current.

4. The apparatus according to claim 3, wherein the direct electric current pulses at a frequency that is a sub-multiple of a resonating frequency of the liquid.

5. The apparatus according to claim 1, wherein the electric current is an alternating electric current.

6. The apparatus according to claim 5, wherein the alternating electric current has a variable voltage and a variable frequency.

7. The apparatus according to claim 5, wherein a frequency the alternating electric current is a sub-multiple of a resonating frequency of the liquid.

8. The apparatus according to claim 1, where each of the at least one vent is drilled/formed at an angle with respect to a longitudinal axis of the first electrode, the angle being other than 90 degrees, fluidly interfacing the bore and an area outside of the first electrode within the pressure and temperature resistant vessel.

9. The apparatus according to claim 8, where the angle aims towards a flow of the fluid within the bore, reducing flow of the fluid from the bore to an area outside of the first electrode in absence of back pressure.

10. The apparatus according to claim 1, wherein the first electrode is electrically and physically interfaced to a holder, the bore also passing through the holder; and wherein each of the at least one vent is drilled/formed in the holder, each of the at least one vent fluidly interfacing the bore and an area outside of the holder within the pressure and temperature resistant vessel.

11. The apparatus according to claim 10, wherein each of the at least one vent is drilled/formed in the holder at an angle aimed towards a flow of the fluid within the bore, thereby reducing flow of the fluid from the bore to an area outside of the holder in absence of back pressure.

12. A method of producing a combustible gas, the method comprising:
    at least partially filling a pressure and temperature resistant vessel with a liquid, the vessel having a first electrode and a second electrode held within the vessel and submerged within the liquid, the first electrode having a bore passing longitudinally through the first electrode;
    at least one vent formed in a wall of the first electrode, the at least one vent fluidly interfacing the bore and an area outside of the first electrode within the pressure and temperature resistant vessel;
    delivering an electric current to the electrodes;
    creating an arc between the first electrode to the second electrode;

flowing the liquid through the bore, the liquid exiting the bore at the arc;

the arc producing a combustible gas; and after the combustible gas percolates to the surface of the liquid, collecting the combustible gas.

13. The method of claim 12, wherein where each of the at least one vent is drilled/formed at an angle of less than 90 degrees with respect to a longitudinal axis of the bore in the first electrode, fluidly interfacing the bore and an area outside of the first electrode within the pressure and temperature resistant vessel.

14. The method of claim 12, where each of the at least one vent is drilled/formed in a holder, the holder electrically and physically interfaced to the first electrode, the bore also passing through the holder, each of the at least one vent fluidly interfacing the bore and an area outside of the first electrode within the pressure and temperature resistant vessel.

15. The method of claim 12, wherein, upon combustion of the combustible gas, temporarily flowing of the fluid back into the bore and exiting the at least one vent.

16. An apparatus for producing usable energy comprising:

a pressure and temperature resistant vessel at least partially filled with a liquid;

two electrodes held by two electrode holders within the vessel and submerged within the liquid, a bore passing longitudinally through a first electrode of the two of electrodes and through an associated electrode holder of the two electrode holders, such that the liquid flows through the bore and exits the bore at an arc formed between the two electrodes by an electric current delivered to the two electrodes; and at least one vent formed in a wall of the first electrode, the at least one vent fluidly interfacing the bore and an area outside of the first electrode within the pressure and temperature resistant vessel;

wherein a combustible gas is produced by the arc and the combustible gas percolates to the surface of the liquid for collection.

17. The apparatus according to claim 16, where each of the at least one vent is drilled/formed in the first electrode at an angle of less than 90 degrees with respect to an axis of the bore, fluidly interfacing the bore and an area outside of the first electrode within the pressure and temperature resistant vessel.

18. The apparatus according to claim 17, where the angle is aimed towards a flow of the fluid within the bore, reducing flow of the fluid from the bore to an area outside of the first electrode in absence of back pressure.

19. The apparatus according to claim 16, wherein the first electrode is electrically and physically interfaced to the associated holder, the bore also passing through the associated holder; and wherein each of the at least one vent is drilled/formed in the associated holder, each of the at least one vent fluidly interfacing the bore and an area outside of the associated holder within the pressure and temperature resistant vessel.

20. The apparatus according to claim 19, wherein each of the at least one vent is drilled/formed in the associated holder at an angle aimed towards a flow of the fluid within the bore, thereby reducing flow of the fluid from the bore to an area outside of the associated holder in absence of back pressure.

* * * * *